United States Patent
Thompson (10) Patent No.: US 7,027,872 B2
(45) Date of Patent: Apr. 11, 2006

(54) VARIABLE ENCRYPTION SCHEME FOR DATA TRANSFER BETWEEN MEDICAL DEVICES AND RELATED DATA MANAGEMENT SYSTEMS

(75) Inventor: David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 273 days.

(21) Appl. No.: 10/620,497

(22) Filed: Jul. 16, 2003

(65) Prior Publication Data

US 2005/0261934 A1    Nov. 24, 2005

Related U.S. Application Data

(62) Division of application No. 09/821,518, filed on Mar. 30, 2001, now Pat. No. 6,622,050.

(60) Provisional application No. 60/193,881, filed on Mar. 31, 2000.

(51) Int. Cl.
*A61N 1/08* (2006.01)
(52) U.S. Cl. .......................... 607/60; 128/903
(58) Field of Classification Search ............... 128/903; 607/30–32, 59–60, 1–2
See application file for complete search history.

(56) References Cited

U.S. PATENT DOCUMENTS

| | | | | |
|---|---|---|---|---|
| 5,354,319 A | | 10/1994 | Wyborny et al. ............... | 607/32 |
| 5,458,122 A | * | 10/1995 | Hethuin ....................... | 600/509 |
| 5,683,432 A | | 11/1997 | Goedeke et al. ............... | 607/32 |
| 6,250,309 B1 | | 6/2001 | Krichen et al. ............... | 128/899 |
| 6,298,255 B1 | | 10/2001 | Cordero et al. ............... | 600/372 |
| 6,298,271 B1 | | 10/2001 | Weijand ....................... | 607/60 |
| 6,363,282 B1 | | 3/2002 | Nichols et al. ............... | 607/30 |
| 6,385,593 B1 | | 5/2002 | Linberg ....................... | 705/28 |
| 6,386,882 B1 | | 5/2002 | Linberg ....................... | 434/262 |
| 6,411,851 B1 | | 6/2002 | Winkler ....................... | 607/30 |
| 6,418,346 B1 | | 7/2002 | Nelson et al. ................. | 607/59 |
| 6,424,867 B1 | * | 7/2002 | Snell et al. ................... | 607/31 |
| 6,442,432 B1 | | 8/2002 | Lee ............................. | 607/59 |
| 6,442,433 B1 | | 8/2002 | Linberg ....................... | 607/60 |
| 6,471,645 B1 | | 10/2002 | Warkentin et al. ........... | 600/300 |
| 6,473,638 B1 | | 10/2002 | Ferek-Petric ................ | 600/523 |
| 6,480,745 B1 | | 11/2002 | Nelson et al. ................. | 607/60 |
| 6,497,655 B1 | | 12/2002 | Linberg et al. ............... | 600/300 |
| 6,564,104 B1 | | 5/2003 | Nelson et al. ................. | 607/60 |
| 6,599,250 B1 | | 7/2003 | Webb et al. .................. | 600/483 |
| 6,622,050 B1 | | 9/2003 | Thompson .................... | 607/60 |
| 6,644,321 B1 | | 11/2003 | Behm .......................... | 128/899 |
| 6,650,939 B1 | | 11/2003 | Taepke, II et al. ............ | 607/27 |
| 6,650,944 B1 | | 11/2003 | Goedeke et al. .............. | 607/60 |

(Continued)

*Primary Examiner*—Robert E. Pezzuto
*Assistant Examiner*—Kristen Mullen
(74) *Attorney, Agent, or Firm*—Daniel G. Chapik; Girma Wolde-Michael (57) ABSTRACT

The present invention provides for an encryption apparatus, system, and method in which data from an Implantable Medical Device (IMD) and a data center could be transferred based on a differentiated encryption system. The encryption scheme allows for the differentiation, segregation, and classification of data at required or needed levels of security. Before transfer of the data, either from an IMD or any other part of a support network for the IMDs, the encryption device begins to distinguish the data. The variable data is then classified based on various levels of security having distinct encryption protocols. After classification the data is encrypted based on the data's level of security. The data is then transmitted. Upon being received the data is then segregated based on whether the data is encrypted. The encrypted data is then de-encrypted and interpreted.

13 Claims, 5 Drawing Sheets

U.S. PATENT DOCUMENTS

| | | |
|---|---|---|
| 6,665,565 B1 | 12/2003 | Stomberg et al. .............. 607/31 |
| 6,699,200 B1 | 3/2004 | Cao et al. ................... 600/508 |
| 2001/0031071 A1 | 10/2001 | Nichols et al. ............. 382/115 |
| 2001/0032085 A1 | 10/2001 | Goedeke et al. ............ 704/275 |
| 2001/0039504 A1 | 11/2001 | Linberg et al. ................ 705/3 |
| 2002/0010492 A1 | 1/2002 | Donovan et al. ............... 607/2 |
| 2002/0045804 A1 | 4/2002 | Christopherson et al. ... 600/300 |
| 2002/0077850 A1 | 6/2002 | McMenimen et al. ......... 705/2 |
| 2002/0095093 A1 | 7/2002 | Au et al. .................... 600/509 |
| 2002/0103505 A1 | 8/2002 | Thompson ..................... 607/1 |
| 2002/0198513 A1* | 12/2002 | Lebel et al. ............. 604/891.1 |
| 2003/0061123 A1 | 3/2003 | McMenimen et al. ........ 705/28 |
| 2003/0139785 A1 | 7/2003 | Riff et al. ..................... 607/60 |
| 2004/0006278 A1 | 1/2004 | Webb et al. ................ 600/483 |

\* cited by examiner

VARIABLE ENCRYPTION SCHEME FOR DATA TRANSFER BETWEEN MEDICAL DEVICES AND RELATED DATA MANAGEMENT SYSTEMS

CROSS-REFERENCE TO RELATED APPLICATIONS

This application is a divisional of application Ser. No. 09/821,518, filed Mar. 30, 2001, now U.S. Pat. No. 6,622,050 which claims priority to and the benefit of the filing date of Provisional Patent Application Ser. No. 60/193,881, entitled "Variable Encryption Scheme for Data Transfer between Medical Devices and Related Data Management Systems," filed Mar. 31, 2000, which application is hereby incorporated by reference in its entirety.

FIELD OF THE INVENTION

The present invention generally relates to data management for medical devices. Specifically, the invention relates to an apparatus and method for variably encrypting and transferring of data transmitted between various devices. More specifically, the invention provides for dynamic encryption of patient data, program commands, physician's options and choices, and similar parameters at varying levels of security based on the content and nature of the data.

BACKGROUND OF THE INVENTION

A network of devices having data communications capabilities, that are associated with implantable medical devices (IMDs) has been provided for the administration of IMDs. On the network may be implemented a system and method of bi-directional telecommunications between an expert data center, clinicians, and an IMD programmer device, utilizing various types of network platforms and architecture to implement, in the programmer, distance-based troubleshooting, maintenance, upgrade, information and is administrative services thereby providing an economical and highly interactive system for therapy and clinical care.

The assignee of the present invention has disclosed data management, transfer and archiving schemes relating to IMDs and associated instruments such as a programmer, remote monitor and similar instruments, which are in data communications with the IMDs. The structures and methods of these schemes are generally defined in applications entitled "Medical System Having Improved Telemetry," filed Jul. 19, 1999, Ser. No. 09/356,340, now U.S. Pat. No. 6,298,271; "System and Method for Transferring Information Relating to an Implantable Medical Device to a Remote Location," filed on Jul. 21, 1999, Ser. No. 09/358,081, now U.S. Pat. No. 6,250,309; "Apparatus and Method for Remote Troubleshooting, Maintenance and Upgrade of Implantable Device Systems," filed on Oct. 26, 1999, Ser. No. 09/426,741, now U.S. Pat. No. 6,442,433; "Tactile Feedback for Indicating "Heart Failure Monitor Quick Look Summary For Patient Management Systems," filed Mar. 17, 2000, Ser. No. 60/190,272; "A Universal Interface For Medical Device Data Management," filed Mar. 17, 2000, Ser. No. 60/190,465; "Telepresence Apparatus And Method For Remote Implantable Medical Device Implementation And Management," filed Mar. 24, 2000, Ser. No. 60/192,006; "A Hand-Held Surface ECG and RF Apparatus Incorporated With a Medical Device," filed Mar. 29, 2000, Ser. No. 60/192,943; all of which are incorporated herein by reference in their entirety. Medical Device," filed Dec. 24, 1999, Ser. No. 60/173,083 "Large-Scale Processing Loop For Implantable Medical Devices (IMDs)," filed Dec. 24, 1999, Ser. No. 60/173,079; "Chronic Real-Time Information Management Systems For Implantable Medical Devices (IMDs)," filed Dec. 24, 1999, Ser. No. 60/173,062; "Automatic Voice and Data Recognition For Medical Device Instrument Systems," filed Dec. 24, 1999, Ser. No. 60/173,071 "Central Switchboard to Facilitate Remote Collaboration With Medical Instruments," filed Dec. 24, 1999, Ser. No. 60/173,080; "System Of Notification Of Recalled Components For A Medical Device" filed Dec. 29, 1999, Ser. No. 09/474,694; "A Communications System For An Implantable Device And A Drug Dispenser" Dec. 30, 1999, Ser. No. 09/475,709; "User Authentication In Medical Systems Device," filed Dec. 30, 1999, Ser. No. 60/173,822; "Automated Invoicing Based On Medical System Usage," filed Dec. 30, 1999, Ser. No. 60/173,824; "Responsive Manufacturing and Inventory Control," filed Feb. 4, 2000, Ser. No. 60/180,289; "Information Remote Monitor (IRM) Medical Device," filed Feb. 4, 2000, Ser. No. 60/180,285 "Follow-Up Monitor For Implantable Medical Device," filed Feb. 23, 2000, Ser. No. 60/184,221; "Implantable Medical Device With Multi-Vector Sensing Electrodes," filed Mar. 1, 2000, Ser. No. 60/186,235; "Stimulator For Delivery Of Molecular Therapy," filed Mar. 7, 2000, Ser. No. 60/187,280; "Individualized, Integrated, And Informative Internet Portal For Holistic Management of Patients With Implantable Devices," filed Mar. 15, 2000, Ser. No. 60/189,562; "Heart Failure Monitor Quick Look Summary For Patient Management Systems," filed Mar. 17, 2000, Ser. No. 60/190,272; "A Universal Interface For Medical Device Data Management," filed Mar. 17, 2000, Ser. No. 60/190,465; "Telepresence Apparatus And Method For Remote Implantable Medical Device Implementation And Management," filed Mar. 24, 2000, Ser. No. 60/192,006; "A Hand-Held Surface ECG and RF Apparatus Incorporated With a Medical Device," filed Mar. 29, 2000, Ser. No. 60/192,943; all of which are incorporated herein by reference in their entirety.

Data encryption is a valuable tool for protecting privacy and ensuring data authenticity. Specifically, encryption technology which has wide application in the management of regulated therapy and diagnosis data, is widely used. More particularly, security relating to medical data is important to prevent tampering, modification or data corruption when data is sent over a public network that is potentially subject to eavesdropping and tampering. Even for dedicated lines and other secure data channels, it may be desirable to use encryption technology, such as digital signatures or checksums to ensure the integrity of transmitted messages. Such confirmation by means of digital signatures or checksums may be particularly indicated in patient care, where privacy, accuracy in instructions, either to a human caregiver or to a remote device, may be important. For example, the highest level of security and accuracy may be indicated for patient data on which critical therapy and diagnosis depend. On the other side of the security spectrum, data that is collected by a sensor on a real time basis, for example, an Electrocardiogram (ECG), an electroencephalogram, or an IEGM, may be sent with minimal or no protection and relatively lower accuracy. In addition, the reduction in computing overhead to which real-time data may be subject according to an embodiment of the present invention helps to ensure that no distortion of data, as a function of time, is injected into the real-time physiologic data being transmitted.

Prior art encryption systems are not dynamically adjustable. Further, prior art systems lack selectable encryption devices and methods which are based on the level of security assigned to the data to be encrypted. Additionally, various networks such as the Internet, World Wide Web, and the like do not implement dynamically variable encryption systems. Prior art systems or networks typically implement encryption on a highly granular level. Typically, these prior art systems will either encrypt all of the systems data at either a very high level, an intermediate level, or not at all. There are problems associated with each one of these levels. If one chooses to encrypt all their data with a high encryption level, then the data will be very secure, however, a large amount of bandwidth is needed to transmit the information. If one chooses to encrypt all of their data at an intermediate level, then the amount of bandwidth required decreases, however, the security of the information decreases. Moreover, if no encryption is utilized, then the amount of bandwidth needed is at a minimum, however the information is not secure.

SUMMARY OF THE INVENTION

The present invention provides for an encryption apparatus and method in which data from an Implantable Medical Device ("IMD") and a data center could be transferred based on a differentiated encryption system. The encryption scheme allows for the differentiation, segregation, and classification of data at required or needed levels of security. The present invention relates to an apparatus and method for securely transferring sensitive information, such as patient information, between a programmer and a clinician computer using encryption methods and structure implemented in hardware or software systems to protect the data from eavesdropping, and ensure its authenticity and integrity. Therefore, one aspect of the present invention to provide a method and apparatus to variably encrypt and transfer data sent between various elements of a data system. Another aspect of the present invention is differentiating between data requiring a high level of encryption from data requiring low or no data encryption.

Yet another aspect of the present invention is to provide a high level of encryption to sensitive data to prevent unauthorized use and or modification.

A further aspect of the present invention is to provide a method and apparatus to variably encrypt and transfer data sent between various elements of a data system through various public networks or internetworks such as the Internet.

Another aspect of the present invention is to provide an apparatus and method, which utilizes bandwidth more efficiently by differentiating between different types of data and only encrypting the data when necessary. Before transfer of the data, either from an IMD or any other part of a support network for the IMDs, the encryption device begins to distinguish the data. In an alternate embodiment of the present invention, the encryption scheme may be manually selected according to the preferences of a user, such as a patient. The variable data is then classified based on various levels of security having distinct encryption protocols. After classification the data is encrypted based on the data's level of security. The data is then transmitted. Upon being received the data is then segregated based on whether the data is encrypted. The encrypted data is then decrypted and may be interpreted by a human clinician or forwarded to a analytical system, computer, or medical device.

DETAILED DESCRIPTION

To assist in an understanding of the invention, a preferred embodiment or embodiments will now be described in detail. Reference will be made to the drawings, which are summarized above. Reference numerals will be used to indicate certain parts and locations in the drawings. The same reference numerals will be used to indicate the same parts or locations throughout the drawings unless otherwise indicated.

Figure 1:
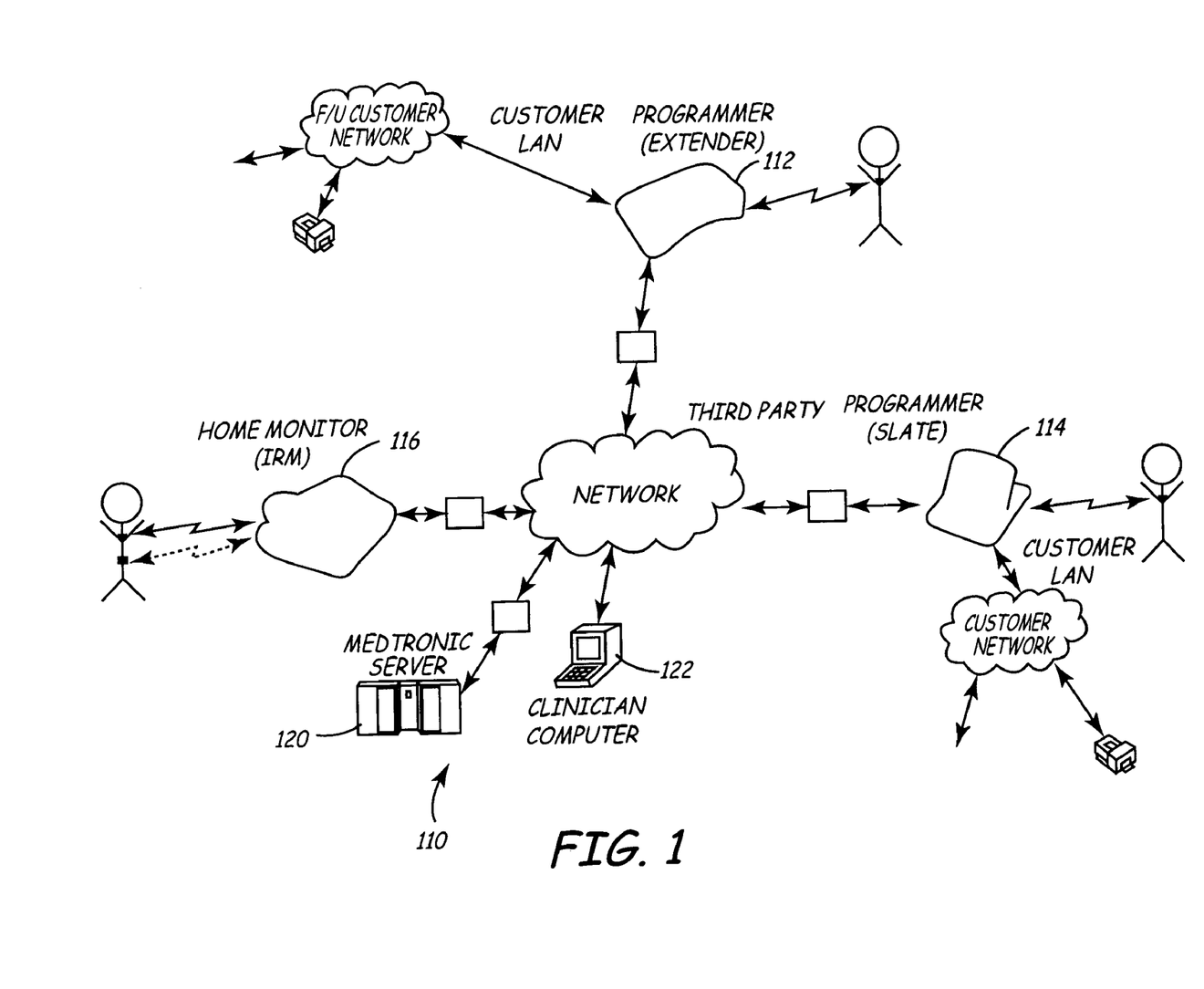
FIG. 1 is a network architecture diagram of a medical device system in which the present invention may be utilized.

With reference to FIG. 1, various types of medical data can be transferred across various storage, memory and server platforms, as provided in the applications listed above assigned in common to the assignee of the instant invention. At each stage of these data transfer operations; security, integrity, and composition may be compromised. Since there is always the potential of eavesdropping on insecure channels or networks, and the potential for corruption of data during the transfer process, there is a need for a high level of security and accuracy for data transfer. This need is of great significance when the data transferred includes patient data, medical device program commands, and physician's options and choices concerning diagnosis and treatment plans. If any of this data is corrupted, this may be insignificant in patient diagnosis and treatment, but may conceivably result in an adverse patient outcome. In addition, regulatory schemes may govern the transmission and communication of such data when it is individually identifiable. Because these possibilities exist, there is a need to encrypt the data being transferred in a medical data management system to prevent tampering, modification, or data corruption through noisy or lossy transmission media. It may even be desireable to provide for non-repudiation of some medical information or communications, such as with regard to reconciliation of conflicting information, which is also possible through asymmetric key encryption schemes.

Nonetheless, there is one significant drawback to data encryption. The more security needed for the data corresponds to a higher level of encryption necessary and thus the more bandwidth needed. Networks are typically limited by bandwidth, i.e., the capability of the network to transmit the impulses which convey the data across network connections, which may be a limitation of a layer of the network protocol, a function of structural resource imbalance in the network, router or other bottlenecks, high traffic, or the limitations of the physical transmission media. Encrypted data typically results in a larger amount of data, from the standpoint of the network, being transferred in comparison to the native data prior to encryption. This is because the encrypted data is a multiplied products of the numerical values of the native data and the encryption key. In addition, message integrity checks, such as the Message Integrity Code (MIC), a secret checksum that cannot be altered without detection, result in additional data relative to the native data. Even data integrity checksums, such as CRC-32, while not technically "encrypted" data, also result in increased bandwidth demands, because the native data is sent in addition to the data integrity checksum.

In considering the encryption and data verification systems discussed above, it is apparent that in addition to bandwidth concerns, the encryption and decryption of data is a relatively computationally-intensive endeavor for computing devices, and adds overhead to processor functioning. Commercial-grade encryption thought suitable for electronic commerce transactions, for example, typically uses a key length exceeding 128 bits. A sufficiently long key length is required to ensure that it remains computationally infeasible to determine a key from a body of cryptotext. Accordingly, the encryption and decryption of data involves the multiplication of data, represented in numeric form, times the other large numbers that constitute the encryption key. Typically, advances in computing power provide that computing devices can cope with increases in key length, while providing that unauthorized decryption is not feasible. However, for some computing devices, particularly medical devices and computer peripherals, this overhead may prove non-trivial, and may result in a slowing down of the processor, transmission-queue backlog, and dropped packets or data. Therefore, high security encryption may prove inconvenient for data security needs, particularly with regard to medical device-related computing equipment. While increases in computer power and speed_help to make this overhead less onerous, these same increases in computing power increase the power of eavesdroppers to decrypt encrypted data, for example, using a 'brute force' or exhaustive computational approach. Accordingly, parties transmitting data and the abstract 'bad guys' may be thought of being engaged in an escalating race with regard to key lengths and computing power. Because of advances in semiconductor technology and chip speeds, by which hardware price/performance ratios are improving about 40% annually, it is generally held that key lengths must grow by at least 1 bit every 2 years. Accordingly, data encryption can be expected to add increasing overhead to data transmission for the indefinite future.

The differentiation scheme provided by the present invention enables a user or device schema to segregate and classify data at required or desired levels of security. This approach enables a system to match a security software scheme that is tailored to the security levels applicable to a data set. The variation in encryption may vary according to the type of data being transmitted, e.g., real-time physiologic signals from an implanted device may not require encryption, while patient records and identifying information will typically be encrypted. Typically, when a regulatory scheme is in place governing the transmission of patient information, there may exist a prohibition on the unauthorized dissemination of medical information that may be tied to an identifiable individual. Therefore, an encryption scheme according to the present invention may provide for encryption of only such data as could lead to the identification by an eavesdropper of the patient to which the data pertains.

Thus patient data, particularly individual patient-identifiable information, program commands to remote programmer devices or implantable device controllers, and physician instructions and preferences, as well as user authentication information, would, by default, be subject to encryption using relatively large key lengths, i.e., using commercial-grade or higher key lengths and encryption schema. In contrast, other data may be regarded as less sensitive, such as real-time sensor, EKG, or IEGM data. This data may by default be sent unencrypted or with minimal encryption. While default settings may be provided for different forms of data, these default values will preferably be subject to change according to user, patient, or clinician preferences, and may also change in response to the quality of network transmission and bandwidth availability. Accordingly, if more bandwidth becomes more or less available, the extent of encryption or the types of data subject to encryption may change. If network traffic becomes noisy or lossy, encryption or checksum integrity verification may automatically be increased so as to provide for protection against garbled data.

The present invention may be expected to speed up the transfer of data and command and control messages to remote medical devices and related peripheral equipment.

This bandwidth and computing overhead demands of encryption often poses the undesirable conflicting demands of security versus efficient transmission throughput. The present invention recognizes and reduces the conflict between these objectives.

Typically, not all data on a network needs encrypting. Each network will have its information it desires to keep secure and its information that does not require any security. Therefore, the present invention promotes economics of bandwidth by classifying various IMD data based on various levels of security having distinct encryption protocols. Thus, data with the highest encryption protocol occupies the largest bandwidth. Alternatively, less critical data may be transmitted with encryption requiring much-reduced bandwidth while data at the lowest security level could be transmitted with no encryption. Asymmetric encryption is slower, i.e., has greater overhead, than symmetric systems by which both parties to a communication share one identical secret key. Accordingly, in one embodiment of the subject invention, a hybrid system is used, by which certain data is encrypted using asymmetric key encryption, part of the data being a symmetric session key for remaining communications in that session or for later sessions, further reducing computing overhead.

In a preferred embodiment of the present invention, a system may be implemented with dynamic configuration of levels of encryption based on the level of risk associated with the data being transmitted. The invention enables, inter alia, data classification, aggregation, and dissemination based on perceived risk levels for secure transfer of data across remote systems in various sized medical data management environments.

Preferably, the invention is implemented in a manner to provide dynamically variable, or "on-the-fly" encryption of transmitted data, especially medical device and patient physiology data between various nodes in a data communications network, such as a medical device "LINK" system, as described in the earlier-referenced patent applications assigned in common to the assignee of this application.

FIG. 1 depicts an implantable medical device communication network generally at 110, as may be implemented according to the earlier referenced patents assigned in common with this application. The variable encryption according to the present invention may be implemented by several of the IMD interface devices utilized in the network, including various types of programmers and instruments, such as, without limitation, Extender 112, Slate 114, or Home Monitor 116. In addition, the variable encryption may be implemented by IMD manufacturer server 120, or clinician computer 122. Each of the interface devices and computing devices would support both a software implementation of the present invention, or a built-in or peripheral hardware implementation of the present invention, as described with reference to FIG. 2.

Figure 2:
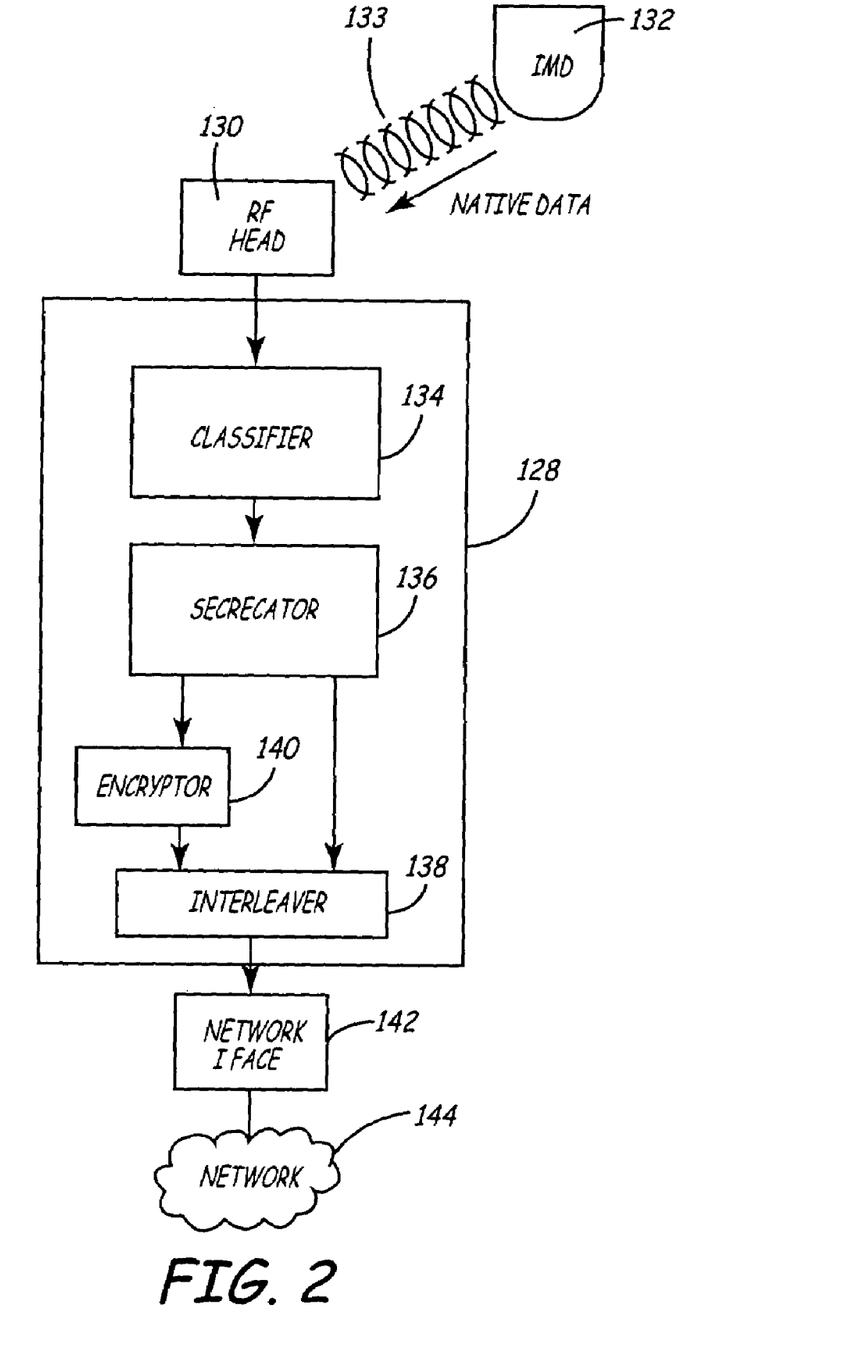
FIG. 2 is a block level diagram of a variable encryption device.

With reference to FIG. 2, a block diagram of the variable encryption assembly is shown. This may be implemented as a hardware component device 128, or as software modules, the software being installed on an interface device to the IMD support network of FIG. 1. An input is received via RF head 130 from IMD 132. The data communication pathway 133 may also be implemented over a physical network connection, with the IMD being replaced by a interface device such as 112, 114, 116, or 118, or computing devices 120 or 122 in FIG. 1 or a data management system or database. Once the data is received into device 128, the classifier 134 determines what type of information the data represents and then outputs the data to the segregator 136. The segregator 136 then separates the data based on preset or user-defined security levels. The preset levels determine what information is encrypted and at what level of encryption. For example, real-time patient monitoring equipment transmissions, which do not individually identify a patient and for which instantaneous data variation is not critical, may be passed directly to interleaver 138. After the data for encryption is segregated it is then outputted to encryptor 140, which encrypts the data at varying levels depending on preset or user-defined level of security. After the data is encrypted it is transmitted to interleaver 138, for placement into the output data stream to network interface 142 for routing to its respective destination of a node on network 144, e.g. a particular IP or other network address. Preferably, data processed through encryptor 140 will be tagged, e.g., with a dummy variable or set bit, to indicate to the recipient that the data is subject to the encryption scheme in place, as discussed herein. Each of the devices 134, 136, 140, or 138 may be implemented as separate software modules rather than hardware devices, for which purposes FIG. 2 may be interpreted as a software architecture diagram.

Figure 3:
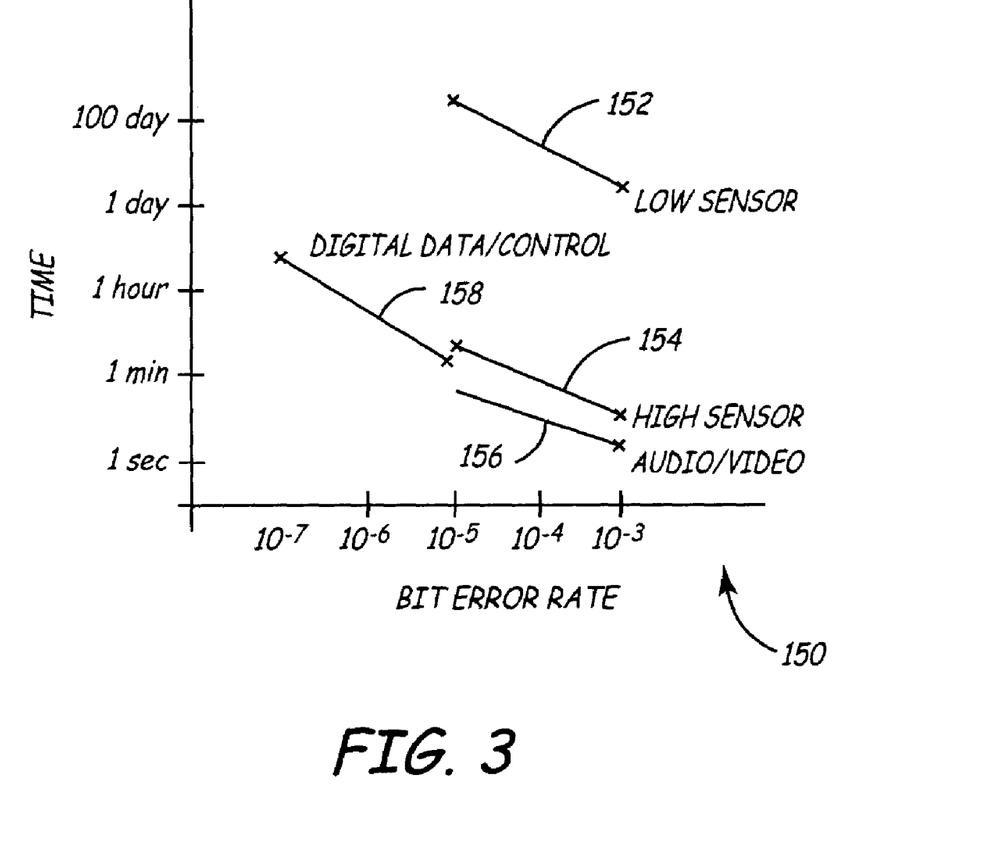
FIG. 3 is a graphical representation of various types of data which may be transmitted in a network system such as that in FIG. 1, showing typical error rates.

With reference to FIG. 3, a pictorial representation of the various medical data that can be transferred along various networks is shown by graph 150. The data includes encrypted, variably encrypted, and un-encrypted data; together with the corresponding bit error rates, defined as the probability of a error occurring in the transmission of a bit, are shown for various types of medically-related data. The medical data may include, for example, low sample rate sensors along range 152, having sample rates on the order of approximately 1 sample per minute. These may include parameters such as oxygen saturation level and blood pressure, for example. These data have a bit error rate on the order of $10^{-3}$ to $10^{-5}$, respectively; and thus may typically be transmitted anywhere between one and 100 days before an error occurs.

Higher sampled sensor signals depicted by range 154, having approximately 512 samples per second, such as electrocardiogram, cardiac flow, and contractility, for example, may be transmitted for between 15 seconds to about 20 minutes before an error occurs with bit error rates in the same range of $10^{-3}$ to $10^{-5}$. Audio/video streaming data transmissions, range 156, in the range of 1.5–3 KHz or 0.25–0.5 KHz compressed, may be transmitted with errors every 5 to 50 seconds with no appreciable degradation of performance and/or function. Digital data, shown by range 158, such as diagnostic counters, programmed parameters, and control variables, may be transmitted for 20 minutes before an error occurs at $10^{-7}$ bit error rate. Using various error correction/detection methods can increase the above mentioned bit error rates. The mean error times may be taken into account dynamically in determining whether performing a checksum or other integrity check would be warranted, considering the importance of instantaneous accuracy in the parameter being transmitted. The mean error rate, expected time between errors, the criticality of the information to patient care and outcome, and volume of native data as a function of time will preferably all be taken into account in determining the encryption level suitable to any given medical data.

Dynamically variable encryptions could also be implemented to manage data from a diverse network of medical devices, as shown in FIG. 1 Thus the present invention would not be limited to simply to medical data management networks, but instead could be implemented on any network. The present invention could be extended to interact between various networks or internetworks, including public networks such as the Internet or the World Wide Web.

Figure 4:
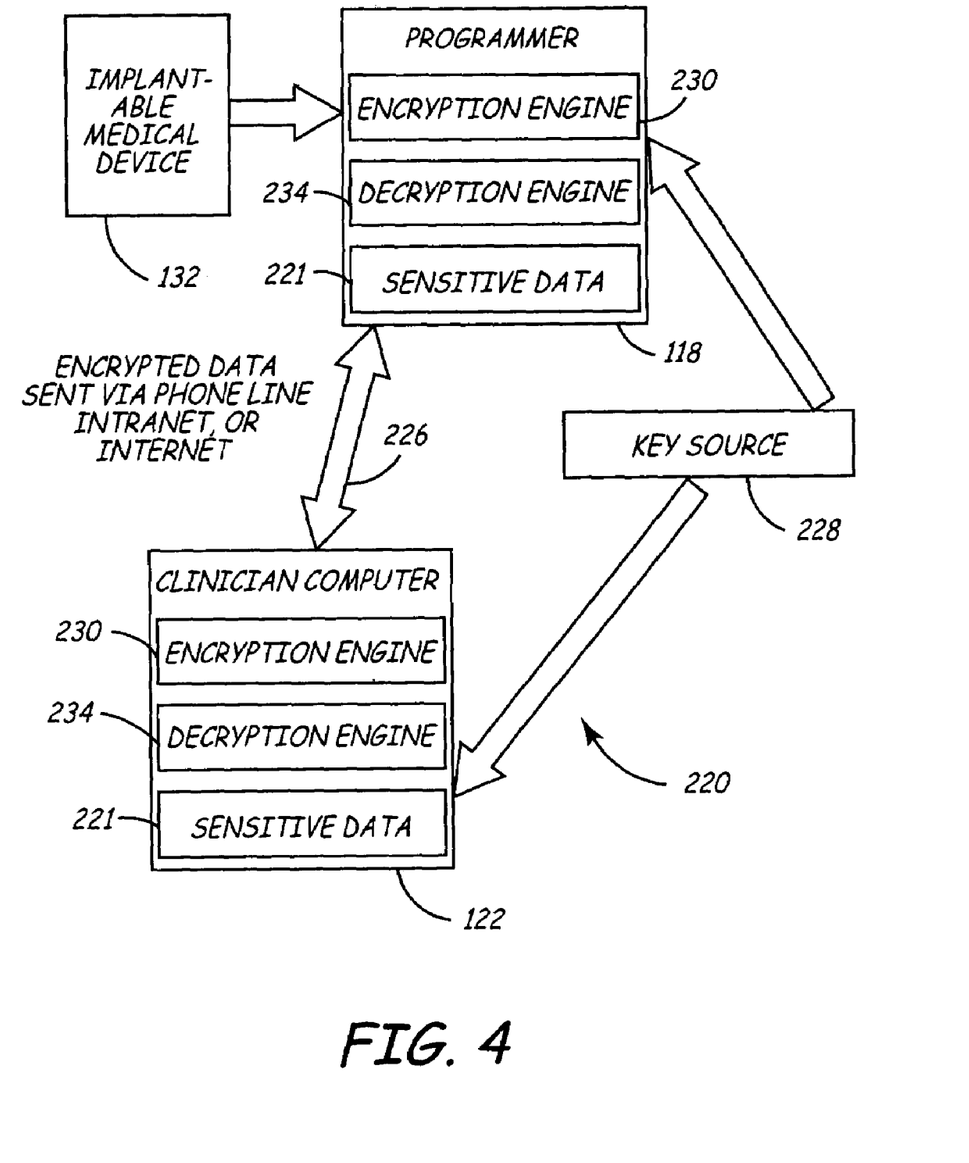
FIG. 4 is a block diagram illustrating an embodiment of a secure data transfer process in accordance with the present invention.

FIG. 4 is a block diagram illustrating one embodiment of a secure data transfer structural scheme in accordance with the present invention, shown generally at 220. In this embodiment, sensitive information 221 (such as patient information) is transferred in encrypted form from IMD any one of the programmers and instruments (112, 114, 116) or similar remote device to remote expert data center or clinician computer 122 across data communications media/connection 226. While a representative use of the present invention is illustrated using communications between Programmer (112, 114, 116) and clinician computer 122, any combination of clinician devices, IMD interface devices, central database or expert system servers, medical device personnel personal computers or servers, and patient monitoring equipment, or any other data transmission device may be used in accordance with the present invention. In the illustrative example, Programmer (112, 114, 116) may be any instrument capable of obtaining, storing, and transmitting medical and administrative information, including sensitive information 221. Programmer (112, 114, 116) is capable of being coupled to one or more IMDs 132. IMD 132 obtains certain information, possibly including sensitive information 221 from the patient, then transfers the patient information to programmer (112, 114, 116). Data communication media 226 could be configured to include a telephone line connection, a direct network connection, an intranet connection, an internet connection, wireless LAN, fiber optic network a satellite connection, a laser or infrared system, any other suitable network protocol connection, or a combination thereof.

Key source 228 provides both programmer (112, 114, 116) and clinician computer 122 with encryption/decryption keys for encrypting/decrypting sensitive information 221. In one embodiment of the invention, key source 228 distributes symmetric encryption/decryption keys. In another embodiment of the invention, key source 228 distributes asymmetric keys (i.e., pubic/private keys). If the encryption/decryption algorithms employed by the invention are standard algorithms known to the public, additional security measures must be taken in the disbursement of the keys from key source 228 to programmer (112, 114, 116) and 122 in order to ensure privacy. In addition to sensitive patient information, the invention may also securely transfer other forms of sensitive information 221, including physician data, customer data, and/or manufacturer data to remote export data center 122. If programmer (112, 114, 116) is transmitting real-time patient physiologic information relayed from an implanted IMD, or is transmitting other information that cannot be identified to an individual, a clinician monitoring or attending computer 122 may select that data be sent in an unencrypted form; which instruction may be sent to programmer (112, 114, 116). Preferably, this instruction to cease transmitting in encrypted mode will itself be encrypted, to provide authentication of the command and prevent a false instruction to this effect by an eavesdropper accessing communication media 226. Alternatively, programmer (112, 114, 116) may be programmed to transmit all real-time physiologic data in an unencrypted form, where this would not subject patient-identifiable information to disclosure.

Before sensitive information 221 is transmitted across data communication media 226, sensitive information 221 is encrypted by encryption engine 230. Encryption engine 230 may be implemented in hardware or software, although may preferably be implemented in software to allow for ease of upgrades to different algorithms, key lengths, and key variation. Encryption engine 230 is a monolithic representation of the hardware device or software implementation of device 128 of FIG. 2. Encryption engine 230 encrypts sensitive information 221 by use of an encryption algorithm and a key. In essence, encryption engine 230 converts sensitive information 221 to a random scrambled message. Encryption engine 230 produces different encrypted scrambled messages depending on the specific value and format of the encryption key. Various encryption algorithms may be utilized within the framework and context of the invention. In one embodiment, the invention utilizes a symmetric key cryptography type algorithm (i.e., the same key is used by programmer (112, 114, 116) and clinician computer 122 to encrypt and decrypt sensitive information 221). Examples of symmetric key cryptography types include Data Encryption Standard (DES) and International Data Encryption Algorithm (IDEA). In another preferred embodiment, the invention utilizes a public key/private key cryptography encryption type algorithm (i.e., different keys are used by programmer (112, 114, 116) and clinician computer 122 to encrypt and decrypt sensitive information 221). Examples of public key cryptography encryption types include the Rivest, Shamir, Adleman algorithm (RSA) and Pretty Good Privacy (PGP). In one embodiment of the subject invention, encrypted communications are effected using a session key, applicable to a single communication session between a device, such as programmer (112, 114, 116), and clinician computer or data center 122. Under this embodiment, encrypted information may be sent after encryption with the session key as a virtually tunneled communication, while other less sensitive or real-time information may be sent in plain-text or native form. In addition to encryption, encryption engine 230 may implement a non-encrypted message integrity checksum, e.g., CRC-32, or a key based MIC.

In one embodiment of the invention, encryption engine 230 also adds a digital signature to sensitive information 221 transmitted by programmer (112, 114, 116). As stated earlier, digital signatures are useful in validating the authenticity of a communication. A digital signature can be used in conjunction with a message containing sensitive information 221 by first creating a message digest (a 128 bit hashed representation of a message) with the sender's (e.g., programmer 112, 114, 116) private key, attaching the message digest to the message, then encrypting both the message digest and the message with the recipient's (e.g., clinician computer 122) public key. The recipient reverses these steps, first decrypting the message with the recipient's private key, then decrypting the signature with the sender's public key.

After sensitive information 221 has been encrypted, the encrypted sensitive information is transmitted to clinician computer 122 via data communications media 226. In alternate embodiments, data communication media 226 is implemented via a telephone line connection, an intranet connection, an internet connection, wireless LAN, fiber optic network, a satellite connection, one or more satellite connections, or a combination thereof. Data communication media 226 may be exposed to security vulnerabilities, for example, during the transmittal of sensitive information 221 from programmer (112, 114, 116) to clinician computer 122. By encrypting sensitive information 221 before transmission, the confidentiality of the information is preserved.

Clinician computer 122 receives the encrypted sensitive information 221 transmitted by programmer (112, 114, 116). In one embodiment of the invention, clinician computer 122 is a second remote medical instrument 221. Decryption engine 234 resides on clinician computer 122, and decrypts the encrypted sensitive information using a decryption algorithm corresponding to the encryption algorithm and a decryption key corresponding to the encryption key that was used to originally encrypt the message. The output of decryption engine 234 is the original, unencrypted sensitive information 221.

Another embodiment of a secure data transfer structural scheme in accordance with the present invention may involve the transfer of encrypted sensitive information from clinician computer 122 to remote instrument 118. This sensitive or critical information may include, for example, IMD instructions or IMD software upgrades.

In this embodiment, simply the reverse of that depicted in FIG. 4, a clinician computer includes an encryption engine, such as that depicted in FIG. 2, for encrypting sensitive information prior to transfer to a programmer via a data communications media/connection. In alternate embodiments, data communication media is implemented via a telephone line connection, an intranet connection, an internet connection, a satellite connection, a constellation of satellite connections, or any combination thereof. The programmer includes a decryption engine for decrypting encrypted sensitive information after encrypted sensitive information has been transferred by clinician computer. The key source provides both programmer and clinician computer with encryption/decryption keys for encrypting/decrypting sensitive information.

This embodiment of the invention is useful when sensitive information, such as patient data, manufacturer data, or operational data, needs to be securely transferred from clinician computer to programmer. For example, a patient monitored by a first programmer may moves to a different part of the country, and switches health care providers. Sensitive information from the patient can first be transferred from the first programmer to clinician computer, as previously illustrated in FIG. 4. Then, sensitive information can be transferred from clinician computer to a second programmer at the new health care provider. Accordingly, sensitive information can be quickly and securely transferred between two or more programmers, via clinician computer.

In another application of the invention, the manufacturer of programmer (112, 114, 116) may wish to update software applications or other manufacturer specific information on programmer (112, 114, 116). Since manufacturer specific information may include sensitive, proprietary information such as software updates or new software modules, it is imperative to the manufacturer that this sensitive, proprietary information be carefully protected. Rather than manually installing the manufacturer updates at a programmer location (which may be time consuming depending on the location of the programmer), the invention enables the secure transfer of manufacturer updates using the various encryption techniques or equivalent structure and methods disclosed herein.

Preferably, the invention will be implemented with bi-directional data transmission of encrypted sensitive information between clinician computer 122 (or other network node) and programmer (112, 114, 116) (or other IMD interface).

In the preferred embodiment, programmer (112, 114, 116) contains both encryption engine 230 and decryption engine 234. Similarly, clinician computer 122 contains both encryption engine 230 and decryption engine 234. Key source 228 provides both programmer (112, 114, 116) and clinician computer 122 with encryption/decryption keys for encrypting/decrypting sensitive information 221 residing on programmer (112, 114, 116) and/or clinician computer 122. Sensitive data is transferred between programmer (112, 114, 116) and clinician computer 122 via data communication media 226. In alternate embodiments, data communication media 226 is implemented via a telephone line connection, an intranet connection, an internet connection, wireless LAN, fiber optic network, a satellite connection, a constellation of satellite connections, or any combination thereof.

In one application of the embodiment shown in FIG. 4, direct transfer of encrypted sensitive information 221 can occur directly between two or more programmers 118. In other words, clinician computer 122 can be a second programmer. Since, in this example, each programmer (112, 114, 116) supports bi-directional secure data transfer (i.e., includes both an encryption engine and a decryption engine), a separate clinician computer 122 is no longer needed to support communications between two or more programmers 222.

FIG. 6 is a flow chart illustrating a method for securely transmitting sensitive patient information from programmer (112, 114, 116) to clinician computer 122 in accordance with the invention, as shown generally at 280. The method begins by generating a first encryption key for distribution to programmer 222, as shown at step 282. At step 284, a second encryption key is generated for distribution to clinician computer 122. Both the first encryption key and the second encryption key are generated by key source 228, shown in FIGS. 5–7. A number of different previously discussed algorithms may be used to generate the first encryption key and the second encryption key. In one embodiment of the invention, the first encryption key and the second encryption key are the same (i.e., symmetric key encryption). In another embodiment of the invention, the first encryption key and the second encryption key are different (i.e., public/private key encryption). In both embodiments, the first encryption key and the second encryption key are related so that an encrypted file produced by the first encryption key may be decrypted by the second encryption key.

Figure 5:
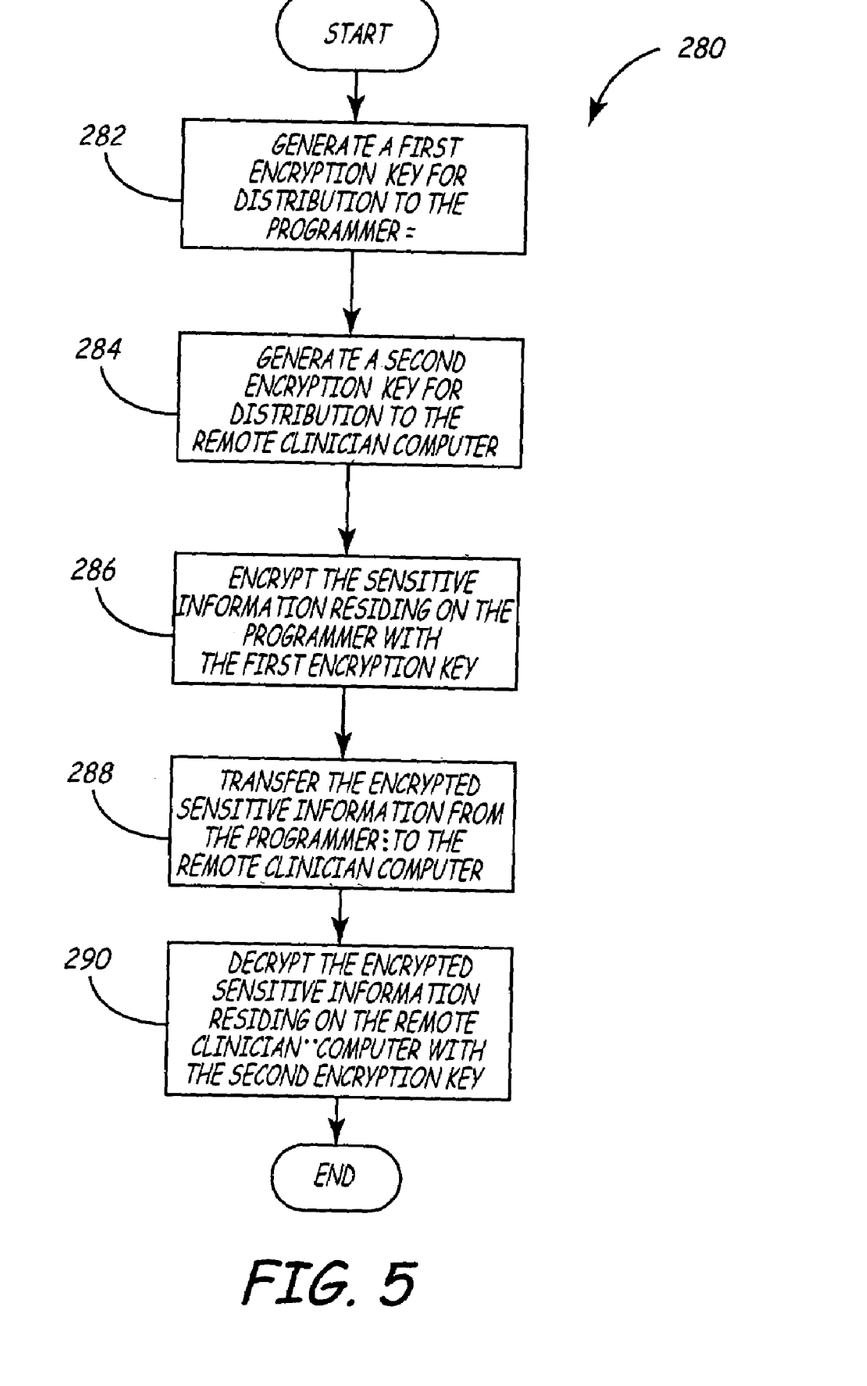
FIG. 5 is a flow chart illustrating a method for securely transmitting sensitive information from a programmer to a computer in accordance with the present invention.

At step 286, sensitive information, after being designated or segregated from non-sensitive data, such as real-time monitoring data residing on programmer (112, 114, 116) is encrypted with the first encryption key. An encryption algorithm resident on programmer (112, 114, 116) takes sensitive information 221 and the first encryption key as inputs and produces a file containing the encrypted sensitive information as an output.

Next, encrypted sensitive information 221 is transferred from programmer (112, 114, 116) to the clinician computer 122 via. data communication media/connection 226, as shown in step 288. In alternate embodiments, data communication media/connection 226 is accomplished via a telephone line connection, an intranet connection, an internet connection, wireless LAN, fiber optic network, a satellite connection, a constellation of satellite connections, a global positioning system (GPS) connection, or any combination thereof. As stated earlier, data communication media/connection 226 may experience security vulnerabilities which compromise the security of sensitive information 221 as the information is transmitted from programmer (112, 114, 116) to clinician computer 122. By encrypting sensitive information 221 before transmission, the confidentiality of the information is preserved during transmission on data communication media/connection 226.

Finally, encrypted sensitive information 221 now residing on clinician computer 122 is decrypted with the second encryption key, as shown at step 290. Decryption engine 234 takes encrypted sensitive information 221 and the second encryption key as input, and generates the original, unencrypted sensitive information 221 for use by clinician computer 122.

It will be appreciated that the present invention can take many forms and embodiments. The true essence and spirit of this invention are defined in the appended claims, and it is not intended that the embodiment of the invention presented herein should limit the scope thereof.

What is claimed is:

1. A computerized method of securely transferring data, including sensitive information, between an IMD and a remote information node over a computer network, the method comprising:
   generating an encryption key for distribution to an IMD interface device;
   generating a decryption key for distribution to the information node;
   transferring data from the IMD to the IMD interface device;
   encrypting the sensitive information, transmitted form the IMD and residing on the IMD interface device, with the encryption key;
   transferring the encrypted sensitive information from the IMD interface device to the remote information node, and
   decrypting the encrypted information residing on the remote information node with the decryption key.

2. The method of claim 1 wherein said data includes one of and a combination of physiological data, cardiac data, neurological data, patient data, therapy data, diagnostic data and device data.

3. The method of claim 2 wherein said data is transferred based on differentiated encryption scheme.

4. A network communications system linking an IMD to an information node via a secure medical information exchange network, comprising:
   at least one key source in data communication with an IMD interface device and with the information node for transmitting an encryption key to the IMD interface device and a decryption key to an expert-data center;
   an encryption engine residing within the IMD interface device for performing data modification that provides encrypted sensitive information information using the encryption key;
   data communication means between the IMD Interface and the medical information exchange network;
   and a decryption engine residing within the information node having means to decrypt the encrypted sensitive information using the decryption key.

5. The network communications system of claim 4, wherein the information node is a clinician computer.

6. The network communications system of claim 4, wherein the information node is a remote expert system server.

7. The network communication system of claim 4, wherein the encryption engine is adapted to recognize non-real time data for encryption.

8. A network communications system for transmitting IMD instruction information from an information node to an IMD via a secure medical information exchange network, comprising:
- at least one key source in data communication with an IMD interface device and with the Information node for transmitting a decryption key to the IMD interface device and a encryption key to the information node;
- data communication means between the IMD interface and the medical information exchange network;
- an encryption engine residing within the Information node having means for performing data modification of IMD Instruction information; and
- a decryption engine residing within an IMD interface device for performing data integrity confirmation.

9. The network communications system of claim 8, wherein the at least one on key source comprises keys hard coded into the IMD, the IMD interface, and a stored key source residing on the information node, respectively.

10. The network communications system of claim 8, wherein data transmitted from the information node comprises native data with an appended data integrity information.

11. The network communications system of claim 10, wherein the native data comprises IMD instructions.

12. The network communications system of claim 10, wherein the native data comprises IMD software upgrades.

13. The system of claim 4 or 8, wherein the IMD interface is in communication with an IMD implanted in a patient.

* * * * *